US008840304B2

(12) United States Patent
Perez Zarate et al.

(10) Patent No.: US 8,840,304 B2
(45) Date of Patent: Sep. 23, 2014

(54) POSITIONER FOR ULTRA-PORTABLE IMAGING SYSTEM (75) Inventors: Victor Manuel Perez Zarate, Halfmoon, NY (US); Michael Anthony Rumsey, Niskayuna, NY (US); Andrea Marie Schmitz, Niskayuna, NY (US); Jeffrey Wayne Eberhard, Albany, NY (US); Scott Dana Tilton, Alexandria, VA (US); Tobias George Harvey, Lorton, VA (US)

(73) Assignee: General Electric Company, Niskayuna, NY (US)

( * ) Notice: Subject to any disclaimer, the term of this patent is extended or adjusted under 35 U.S.C. 154(b) by 385 days.

(21) Appl. No.: 12/980,392

(22) Filed: Dec. 29, 2010

(65) Prior Publication Data

US 2011/0306864 A1 Dec. 15, 2011

Related U.S. Application Data (60) Provisional application No. 61/354,680, filed on Jun. 14, 2010.

(51) Int. Cl.
*H05G 1/02* (2006.01)
*A61B 6/00* (2006.01)
*A61B 19/00* (2006.01)

(52) U.S. Cl.
CPC ............ *A61B 6/4458* (2013.01); *A61B 6/4405* (2013.01); *A61B 2019/265* (2013.01); *A61B 6/447* (2013.01)
USPC .......................................... 378/198; 378/197

(58) Field of Classification Search
USPC .................................................. 378/193–198
See application file for complete search history.

(56) References Cited

U.S. PATENT DOCUMENTS

| 5,067,145 | A | * | 11/1991 | Siczek et al. | 378/198 |
| 5,428,660 | A | | 6/1995 | Daniel, Jr. | |
| 5,521,957 | A | * | 5/1996 | Hansen | 378/198 |
| 5,586,162 | A | | 12/1996 | Grichnik | |
| 6,716,167 | B1 | | 4/2004 | Henderson et al. | |
| 2007/0133751 | A1 | | 6/2007 | Chicchetti et al. | |
| 2009/0058036 | A1 | * | 3/2009 | Hoepner et al. | 280/267 |
| 2009/0069130 | A1 | * | 3/2009 | Nye et al. | 473/484 |

OTHER PUBLICATIONS

Support and Consumables Handbook, "Medical Materiel Set X-Ray, Light Weight, Diagnostic Portable", U.S. Army Medical Materiel Agency, pp. 1-13, Aug. 2010.

* cited by examiner

*Primary Examiner* — Hoon Song
(74) *Attorney, Agent, or Firm* — Jenifer E. Haeckl (57) ABSTRACT

A flexible, lightweight, easily maneuverable positioner for an imaging system. The positioning system in one example has a cart section with a base frame coupled to one or more wheels. There is a mast extending from the cart section and a linkage assembly coupled to a second end of the mast, wherein the mast is configured to swing about a vertical plane. There is a positioning arm coupled to the linkage assembly, wherein the positioning arm is configured to swing about at least one of a horizontal plane and the vertical plane. An imaging bracket is used to couple to the positioning arm and configured to receive an imaging unit. In one example, the positioner is coupled together by fasteners, wherein the positioner can be assembled and dis-assembled via the fasteners without tools.

21 Claims, 8 Drawing Sheets

POSITIONER FOR ULTRA-PORTABLE IMAGING SYSTEM

CROSS REFERENCE TO RELATED APPLICATIONS

This application claims the benefit of U.S. Provisional application No. 61/354,680, filed Jun. 14, 2010, which is herein incorporated in its entirety by reference.

GOVERNMENT LICENSE RIGHTS

This invention was made with government support under W81XWH-08-2-0185 awarded by U.S. Army. The government has certain rights in the invention.

BACKGROUND

Medical equipment positioners are typically used on portable imaging systems in order to more readily position the imaging apparatus for proper imaging. There are several commercial portable imaging positioners in the market and they can be classified into two general types. The first type consists of a deployable frame with two wheels and legs that extend under the bed for support. An arm with a gas strut helps to position the source. The source position is controlled by the swing of the arm.

The second type provides a rolling base typically with four wheels. In general they do not collapse for easy transport and deployment. The source is mounted either on a fixed arm with limited vertical adjustability, or a swing arm as described herein.

While there are some known medical equipment positioning systems, there continues to be a need for improvements to provide greater flexibility, easier transport and enhanced capabilities. In particular, there is a growing desire for more rugged and robust imaging platforms that can be easily transported to rural areas and military deployments where the floors and imaging territory are non-ideal.

BRIEF DESCRIPTION

In accordance with one exemplary embodiment, a positioner has a cart section with a base frame coupled to one or more wheels, wherein the wheels are resting upon a surface. There is a mast extending from the cart section on a first end and oriented approximately orthogonal from the surface. The linkage assembly is coupled proximate to a second end of the mast and configured to swing about a vertical plane. A positioning arm is coupled to the linkage assembly and configured to swing about at least one of a horizontal plane and the vertical plane. The imaging bracket is coupled to the positioning arm and configured to receive an imaging unit, wherein the positioner is coupled together by fasteners, and the positioner can be assembled and dis-assembled via the fasteners without tools One example is a transportable imaging system, having a cart section with at least one of wheels, rollers or combinations thereof. A mast receptacle is fastened to the cart section and a mast having a lower end and an upper end extends vertically from the cart section. There is a wrist attached proximate the upper end of the mast, with a first beam having a first end and a second end, wherein the first end is attachably coupled to the wrist, the mast configured to extend vertically. A shoulder and elbow are used to form a cylindrical joint coupled to the second end of the first beam. A second beam with a first end and a second end, the first end also coupled to the cylindrical joint, wherein the second beam is rotatable in a horizontal plane. A wrist is coupled to the second end of the second beam, wherein the wrist is also coupled to an imaging bracket. The imaging source is coupled to the imaging bracket.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One embodiment of the disclosed system covers a flexible, lightweight, easily maneuverable means to position an imaging source relative to a patient. Another implementation is for a portable positioner system used in a far forward theatre of military operations or in a rural environment that requires a mobile and robust imaging system. The positioning system according to one embodiment addresses simultaneous characteristics imposed by the scenario as portability, maneuverability, flexibility, and ease of use.

The portability requirements include the size and weight of the positioner assembled and packed in its cases. The ability for easy stacking, handling, and transportation of the cases is a further feature. A further feature is that the assembly and disassembly of the positioner can be accomplished in limited time and with no-tools.

The positioner maneuverability requirements in one example allow a single operator to relocate the system from one bed to another, and from one tent to another. The positioner can maneuver over uneven surfaces, stretch spaces and turn in tight corners, as well as navigate through non-smooth surfaces such as sand and over small curbs.

In one embodiment, the positioner offers the flexibility of quick location of an imaging system such as an x-ray source for anterior-posterior (AP), lateral (LAT), and any OBLIQUE shoots. The orientation of the x-ray source can be changed with ease in both the horizontal and vertical direction with respect to the ground surface upon which the unit rests. A feature of the system is that the operator can perform head-to-toe shots without major re-positioning. The positioner can be located along a bed, without the need of open space underneath the patient, allowing for greater flexibility.

Figure 1:
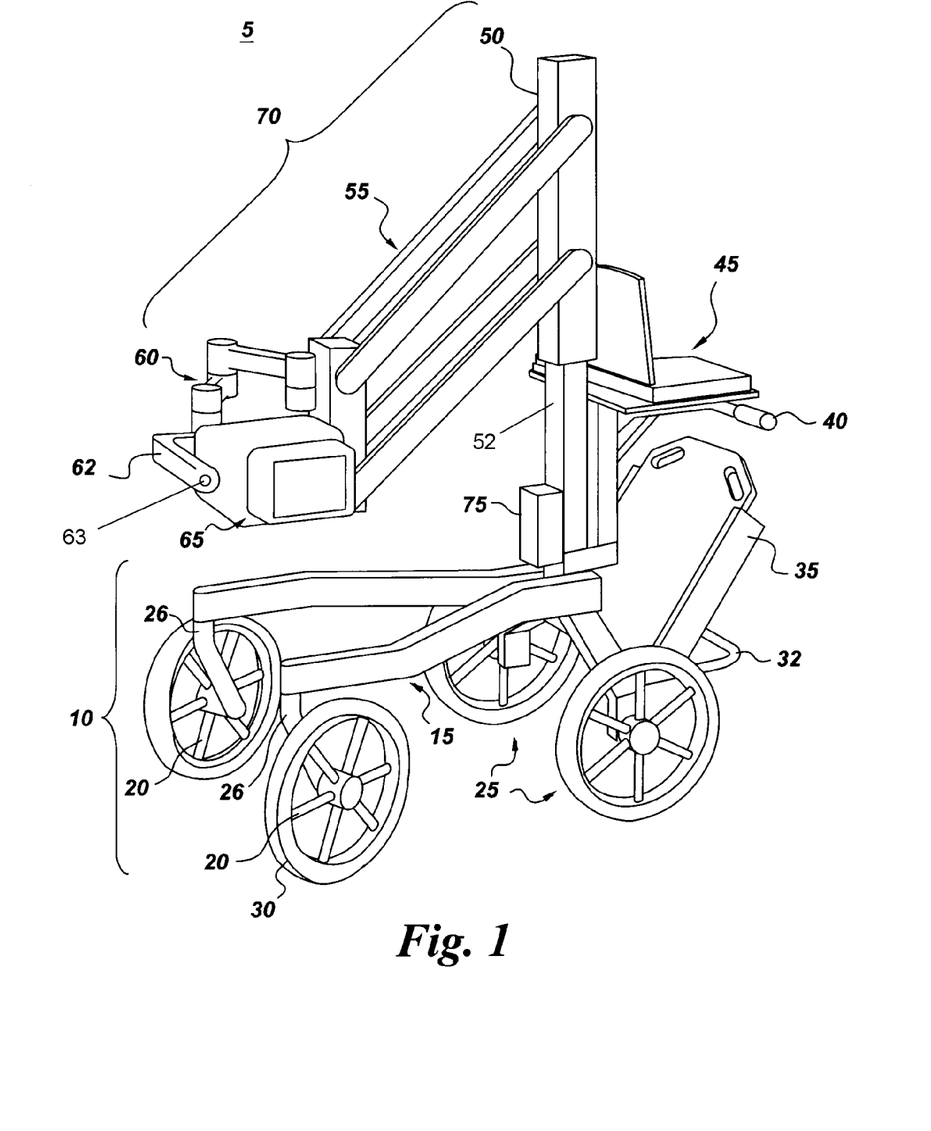
FIG. 1 is a perspective view of a positioner in accordance with an exemplary embodiment.

Referring to FIG. 1, depicting one embodiment, the positioner system 5 includes the cart section 10 that refers to the base frame 15 coupled to one or more wheels, which in one embodiment includes two front caster wheels 20, and two rear wheels 25. In another embodiment the base frame 15 consists of four independent legs that are attached to the mast 50. The wheels 20, 25 in one example are light and have a large diameter with tires 30 for ease of rolling on different floor conditions and surfaces. In one example large width of the tires 30, such as 16 inch×1.75 inch, allows for easier transport over sand and rough surfaces encountered in adverse environments and conditions not typically encountered in domestic hospitals. The front casters 20 can include a locking mechanism to move the positioner 5 in a straight line, to accommodate easy head-to-toe imaging applications. In one example the rear wheels 25 have a mechanism to lock the wheels on uneven terrain. The legs 26 that couple the frame to the wheels 20, 25 can be individual parts assembled to a central component, or can be part of the single base frame 15.

According to one embodiment the wheels 20, 25 are secured to the legs 26 and base frame 15 such that no tools are required for mounting and dismounting. For example, you could utilize a quick release axle to secure the wheels to a forked caster, or use a knob and bushing mechanism 12 such as depicted in FIG. 8B to secure the wheels to the caster or the cart leg.

Additionally the wheels 20, 25 can include shock absorbers (not shown) that can lessen the sharp bounces. Various types of shock absorbers are known in the art including pneumatic, spring, and hydraulic absorbers. In one example the shock absorbers are coupled or integrated with the legs 26 to absorb the bounces of the wheels 20, 25. Alternate embodiments provide for locking hubs (not shown) or similar mechanisms for securing the positioner 5. While the positioner 5 is shown with four wheels with tires, a three-wheeled system having a single front wheel is an alternate embodiment. Likewise, there can be other mechanisms for movement that can be in combination with one or more wheels. For example, rollers can also be used instead of tires as the wheeling mechanism to provide transportability of the positioner. The front legs 26 in one example are attached to the base frame 15 using fasteners such as self-locking pins for ease of assembly. In addition, the rear wheels 25 are coupled using self-locking pins and are easily installed or removed. The wheels in one embodiment are attached using knobs so that they can be removed as needed.

According to another variant, each leg 26 has a pivot at its joint to the system. The front legs collapse in a counterclockwise direction while the rear legs collapse in a clockwise direction. This is a more compact design for storage and transportation with minimum assembly.

To provide power for mobile operation when unconnected to a power source, a power supply 75 is included along with a power supply holder that allows for various numbers and sizes of batteries. Batteries can be electrically coupled to extend imaging operations. In one example the power supply 75 provides ballast to allow for extended operation of the imaging. The power supply 75 in one example is completely portable and includes the AC-DC conversion capability to plug into various forms of AC power sources to operate the positioner imaging and charge the power supply 75.

Another feature on the positioner 5 is the wheelie bar 32 that is used as a lever to allow the front of the positioner 5 to lift up and easily go over bumps and curbs. Putting the operator's foot on the wheelie bar and applying pressure will lift the front of the positioner 5 and the front wheels 20 thereby allowing the unit to go over large bumps and curbs. While conventional imaging systems tend to be deployed in hospitals with flat floors and limited obstacles, wherein the present positioner 5 is deployable in extreme conditions and the wheelie bar aids in transporting the positioner. The wheelie bar 32 in one aspect is mounted to the rear legs of the base frame or the base frame itself and extends outwardly to provide sufficient leverage to lift the front of the positioner 5 when pressure is applied.

There is a detector/phantom holder tray 35 coupled to the base frame 15 in one example that is used for storage of the imaging elements such as the detector and phantom during transport and when not in use. The tray component 35 allows for easy retrieval of the detector and phantom and in one example the tray rests on pins over the wheelie bar 32 and is pivotably positioned from an operating position to a stowed position. The desk and desk support 45 are also attachable via self-locking pins to the mast 50, wherein the entire desk and desk support 45 are removable.

The mast 50 is the central element that supports the source manipulating arm 70 and imaging unit 65, as well as other elements such as the laptop desk 45 and accessories/attachments. In one embodiment the power supply 75 is coupled to the mast 50 instead of the base frame 15. As detailed herein, the mast 50 provides vertical adjustment and otherwise supports the imaging unit 65 for deployment. In one embodiment the mast 50 is telescoping and elevates vertically. Another embodiment the mast 50 is of a fixed length. In another embodiment the mast 50 can be rotated thereby providing two degrees of freedom for the manipulating arm 70. The mast 50 in one example is removeably coupled to the base frame 15 and securely holds the mast 50 to the base frame 15.

One aspect of the coupling of the mast 50 to the base frame 15 is that no tools are required for the attachment, as the mast 50 slides onto a mating receptacle 52 on the base frame 15. Various locking pins (not shown) and mechanical mechanisms secure the mast 50 to the base frame 15. A further aspect includes the mast 50 having a generally square, rectangular or circular shape either hollow or solid that mates with a corresponding mating receptacle. To provide further flexibility, another embodiment includes a hinge (not shown) that allow the mast 50 to be folded into the cart section 10 for storage, and secured vertically for use with a self-locking mechanism. In another aspect, at least the lower portion of the mast is round or cylindrical and mates with a corresponding receptacle of the base frame 15. To provide a rotational movement for the mast 50, one example includes a groove in the receptacle that allows for a matching pin to swivel about the groove, with or without a bearing for ease of movement. Various other attachments can be used to provide such rotational movement of the mast.

As detailed, the manipulating arm 70 provides adjustability in the horizontal plane with respect to the ground surface thereby, for example, extending the imaging unit 65 fully to both sides of a patient on a cart for a LAT shot. It also provides a vertical adjustment capability to provide imaging, for example, of a patient on a low hospital bed as well as a much higher operating table.

The manipulating arm 70 in one embodiment includes a linkage assembly 55 extending from the mast 50 and a positioning arm 60 that provides the flexible movement between the linkage assembly 55 and the imaging unit 65. In one example the linkage assembly 55 provides a vertical movement to adjust the height of the imaging unit 65 as well as an extension capability to extend the reach of the imaging unit 65 and to provide sufficient support for the imaging unit 65 when the positioning arm 60 is extended. For example, in the depicted example the mast 50 extends approximately orthogonal from the ground surface thereby establishing a vertical plane. The linkage assembly 55 is coupled to the mast 50 and provides movement along the vertical plane with respect to the ground surface.

In one example the linkage assembly 55 is a removable, double parallel four bar assembly coupled at the mast 50 by pins such that a pair of the bar assembly members is mounted on opposing sides of the mast 50 so that they are parallel to each other. As an alternative a single parallel four bar mechanism can be used provided it contains enough rotational stiffness. The single parallel four bar mechanism can include one or more additional linkage support members to augment the stiffness. The double parallel four bar riser mechanisms allow the linkage assembly 55 to move in the vertical plane. According to one aspect, the linkage assembly 55 has a vertical travel large enough to extend the imaging unit 65, such as an x-ray source, for both AP and LAT images.

In one example, a gas spring is used to counterbalance the load and assist the user to lift the source. The gas spring in one example is coupled between the middle of the mast on one end and a middle location on either the upper bars or the lower bars of the linkage assembly 55 on the other end. In one example, the gas strut is attached to the upper or lower bars via a pin, in another example it attaches directly to one of the upper or lower bars of the linkage assembly. The gas strut in one example includes a locking feature to fix the position. This locking feature can assist in the assembly and disassembly process as well as holding the linkage assembly 55 in the desired position. A further embodiment of the linkage assembly 55 provides for coupling of the linkage assembly 55 to sockets on the mast 50. According to one example, the four bars of the linkage assembly are configured with end pieces to be inserted into sockets on the mast 50.

At the end of the linkage assembly 55 is a positioning arm 60 that allows for increased maneuverability of the imaging unit 65. In one example the positioning arm 60 is a three member positioning arm including three joints having posts and links to allow for ease of assembly. The joints in one example can be cylindrical joints, locking ball joint, and combinations thereof. In another example at least one of the members of the positioning arm 60 has telescoping capabilites. For example, one or more of the members in the three member positioning arm can employ an inner and outer sleeve configuration such as the telescoping mast, with locking pins or other locking mechanism to provide for telescoping to a fixed length.

In one aspect, a bracket 62 is used to connect the imaging unit 65 with the positioning arm 60, wherein in a further aspect the imaging bracket 62 can also rotate with respect to the positioning arm 60 and the source 65 providing even further maneuverability. The bracket 62 in one example has pins or threaded members 63 that allow for attachment of the imaging unit 65 to the bracket 62. Yet a further embodiment provides for a quick disconnect so that the imaging source 65 is easily detached from the bracket 62 without the use of tools.

The combination of adjustability via the manipulating arm 70 and the positioning arm 60 allows the device 5 to position the imaging unit 65 pointing to any direction as required by the application. The additional adjustability in one aspect that is provided by the bracket 62 augments the flexibility.

According to one example, the positioner system 5 can be entirely assembled/disassembled in a short period of time without the need of external tools. All assembly joints use self-locking pins or knobs to secure the components in place.

Figures 2A, 2B:
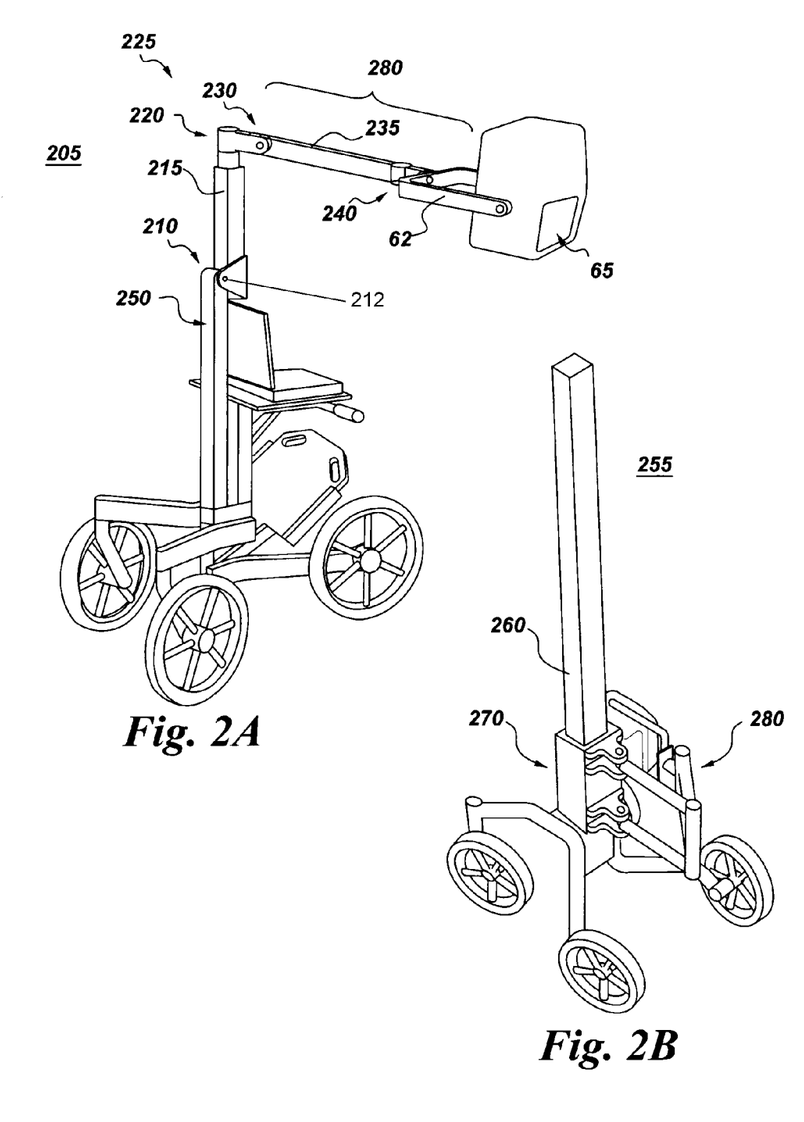
FIG. 2a-2b are perspective views of alternative positioner configurations in accordance with other exemplary embodiments.

Referring to FIG. 2a, a different positioner system 205 is depicted. This embodiment includes a mast 250 attached to the cart section 10. The manipulating arm 225 is formed by straight beams 215, 235 joined by coupling joints, namely waist 210, shoulder 220, and elbow 230. In more particular detail, the linkage assembly 275 includes a first beam section 215 coupled to the mast 250 by a waist 210, which in configured to provide vertical motion of the first beam section 215, wherein the first beam 215 can be raised vertically and a locking pin 212 can retain the desired height. In another example the waist 210 is configured to allow the first beam 215 to be folded for a storage state or unfolded for an operating state. As noted, the linkage assembly 275 provides for an extension of the mast 250 in the vertical plane.

The positioning arm 280 comprises the shoulder 220 and elbow 230 that provides the coupling for the second beam section 235 such that the positioning arm 280 provides for positioning in the horizontal plane. In this example, the shoulder 220 and elbow 230 form a cylindrical joint, wherein the shoulder may or may not have locking capabilities. In one example, the elbow 230 has locking abilities, wherein it may be restricted to 90 degrees rotation and it may have locking capabilities at either or both extreme positions. For illustrative purposes of one example, the linkage assembly 275 allows the imaging unit 65 to be positioned in the upper position for an AP image and in the lower position for a LAT image. The positioning arm 280 pivots the imaging unit 65 to its deployed location. The imaging unit 65 in this example is attached to the manipulating arm 225 at the wrist 240 by the bracket 62, which in one example is a C-shaped bracket. The imaging unit 65 can rotate around the mast 250 by the elbow 230. A fine vertical adjustment can be achieved by adjusting the height of the telescoping mast 250. The wrist 240 in other embodiments can be a cylindrical joint or a locking ball joint.

The positioner system in FIG. 2b provides an example of a vertical sliding mast positioner 255. In this example, a stationary mast 260 is attached to a cart section 10 on a lower end and engages a sliding bracket 270, wherein the sliding bracket 270 is coupled to a positioning arm 280 that is attached to the imaging unit 65. The single stage mast 260 in this design is not telescoping but provides for the full range of vertical travel without the need of additional mechanical components. The sliding bracket 270 slides up and down along the mast 260 such as by rails. In one example, the sliding bracket 270 is locked at any point along the mast 260 such as by locking pins. This configuration provides for an independent vertical source adjustment and horizontal plane positioning via the positioning arm 280. In one example the internal components of the mast 260 includes pulleys or coils provide that assist positioning of the positioning arm 280 and imaging unit 65.

Figure 3A:
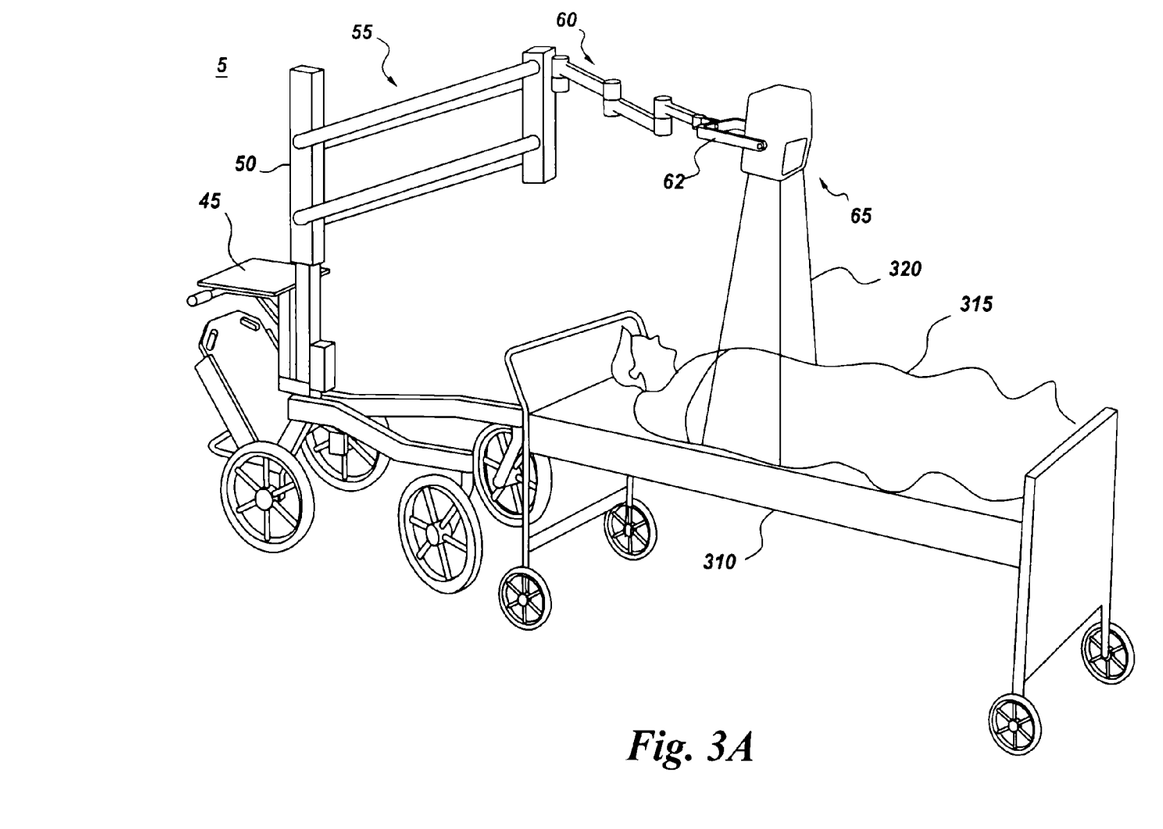
FIG. 3a shows the positioner of FIG. 1 configured for one embodiment of top scan imaging with the positioner situated at the head of the bed.

FIG. 3a shows one imaging example deployed with the imaging unit 65 extended over a table 310 such that the source 65 is positioned to make the appropriate medical imaging, which in this case is a top scan 320. In this example the positioner 5 is able to image from the end of the bed or table 310, extending over the patient 315 to the desired location. The telescoping mast 50 is set to a desired height, the linkage assembly 55 provides further extension and elevation, the positioning arm 60 further extends the imaging unit 65, while the bracket 62 enables the imaging unit 65 to swivel to the scan orientation. An operator (not shown) operates the computer 45 to perform the imaging of the patient 315.

The computer 45 is configured for an operator to perform the appropriate imaging via a user interface such as keyboard, mouse and/or touchscreen. Various other user interfaces such as voice input are also within the scope of the system processing. In certain embodiments, the computer 45 incorporates computer programs having executable on the computer 45 to facilitate the imaging in a manual, semi-automated or automated fashion. The computer programs provide for a user interface that allows less experienced operators to obtain the required imaging. The images from the imaging can be stored on memory coupled to the computer and can also be communicated by wired or wireless modes to deliver the images such as for storage and/or analysis.

Figure 3B:
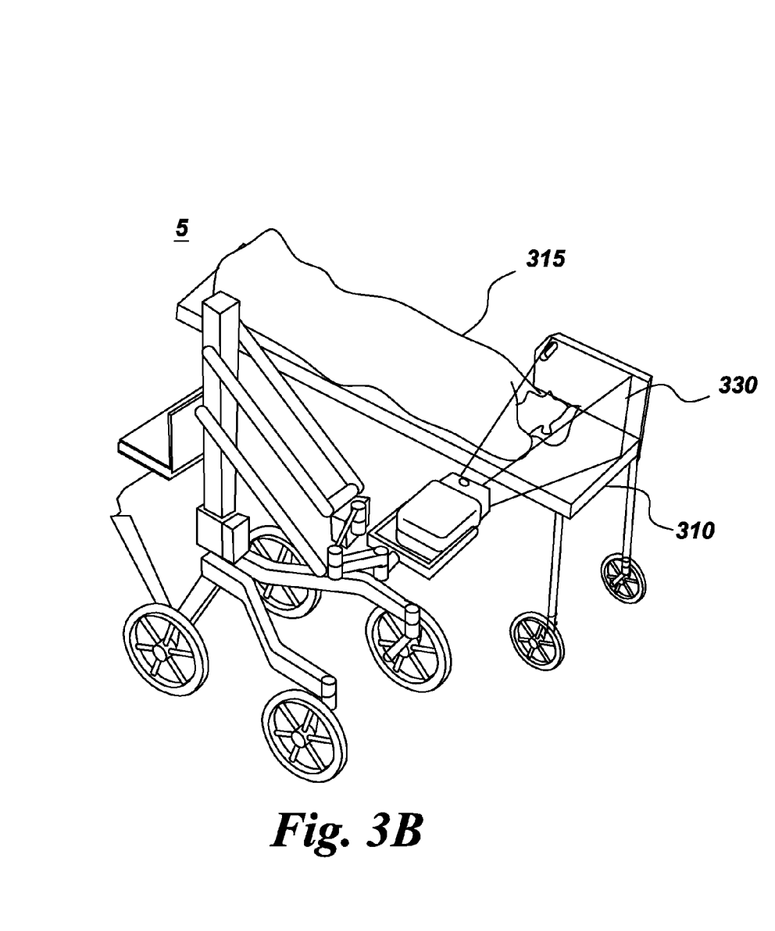
FIG. 3b shows the positioner of FIG. 1 configured for side scan imaging with the positioner situated at the side of the bed.

As shown in FIG. 3b, a further imaging example illustrates the positioner system 5 at the side of the table 310 with the imaging unit 65 performing a side scan 330 of the patient 315. The telescoping mast 50 is lowered to a desired height, the linkage assembly 55 provides further lowering, the positioning arm 60 swivels the imaging unit 65, while the bracket 62 further enables the imaging unit 65 to perform the scan orientation. An operator (not shown) operates the computer 45 to perform the imaging of the patient 315.

Figure 3C:
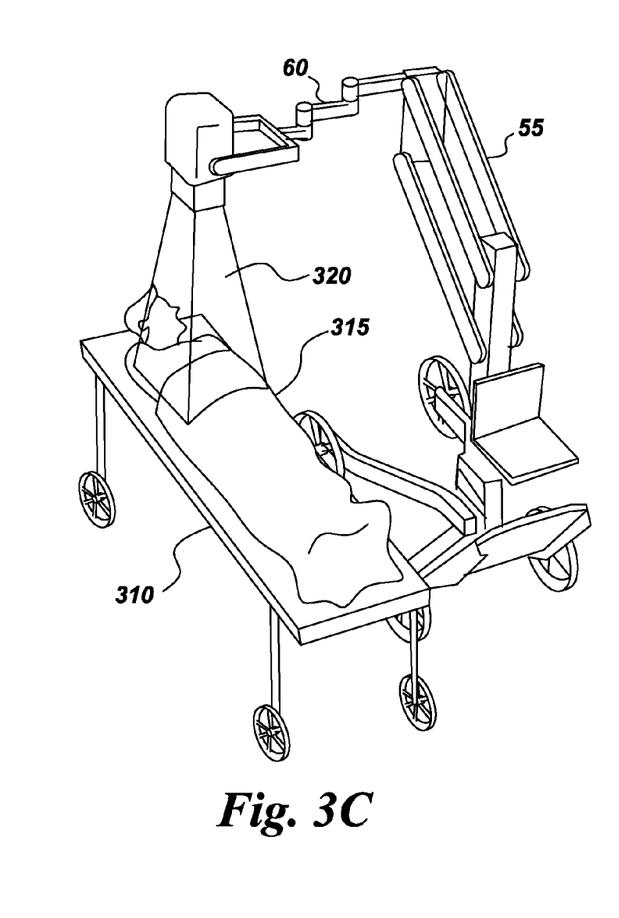
FIG. 3c shows the positioner of FIG. 1 configured for top scan imaging with the positioner situated at the side of the bed.

As shown in FIG. 3c, a further imaging example illustrates the positioner system 5 at the side of the table 310 with the imaging unit 65 performing a top scan 320 of the patient 315. The telescoping mast 50 is lowered to a desired height, the linkage assembly 55 provides further lowering, the positioning arm 60 swivels the imaging unit 65 approximately 90 degrees, while the bracket 62 further enables the imaging unit 65 to perform the scan orientation. An operator (not shown) operates the computer 45 to perform the imaging of the patient 315.

As illustrated, the positioner 5 is easily configured in the Lateral or LAT position as well as the anterioposterior or AP position. This imaging configuration provides medical imaging from a side perspective or a front to back perspective. The source height and horizontal position can be modified to accommodate varied heights and distances.

Figure 3D:
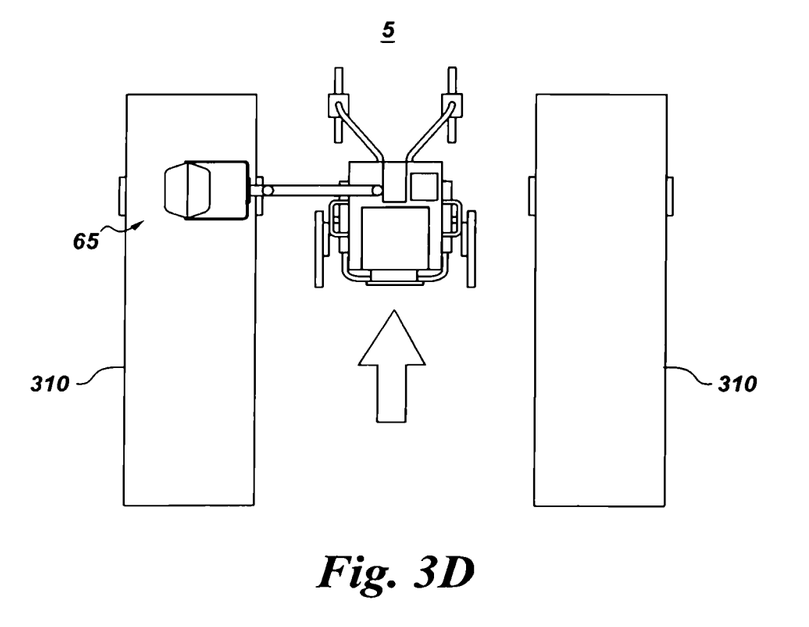
FIG. 3d illustrates the positioner deployed between beds providing imaging capabilities on both sides of the positioner.

One application of the positioner 5 is to accommodate multiple tables 310 such as shown in FIG. 3d. The compact positioner 5 design and the flexibility and positioning of the manipulator arm 70 facilitates imaging in tight conditions for top scans and side scans and the imaging to the beds/tables on both sides of the positioner. The configuration enables easy system repositioning for multiple shot image acquisition alongside the bed without repositioning the imaging source.

Figure 4:
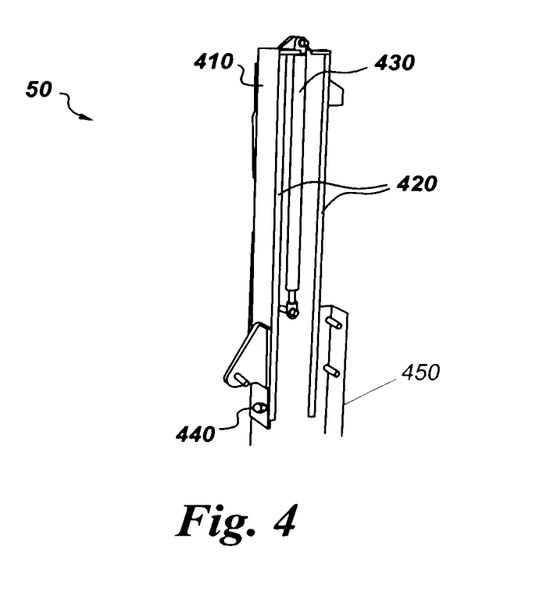
FIG. 4 depicts the internal components of the mast of the positioner according to one embodiment.

Referring to FIG. 4, further details of the mast 50 from FIG. 1 is depicted. In this example, the mast 50 is telescoping and has an inner mast 410 and an outer mast 450, wherein the outer mast slidably engages with the inner mast 410, such as having the outer mast engage with the inner mast via nylon slides 420. The outer mast 450 slides over nylon slides 420 that are secured to the inner mast 410 and provide a smooth surface for the outer mast to slide along. In one example an internal strut 430 helps balance the load that is applied to the mast 50 thereby providing easy adjustment in the vertical direction. One extreme of the strut 430 is attached to the inner mast 410 and the upper extreme of the strut 430 is coupled to the outer mast 450. The strut 410 can be a gas strut, hydraulic strut or mechanical spring. During transportation, the outer mast 450 is locked in the most compact position with a locking screw 440.

The compact position is used for transportation and relocation and for imaging from lower height locations. The extended position is used for most images from the top. In one example, the mast telescopes about twelve inches in the vertical direction thereby extending the reach and height of the imaging unit.

Figure 5:
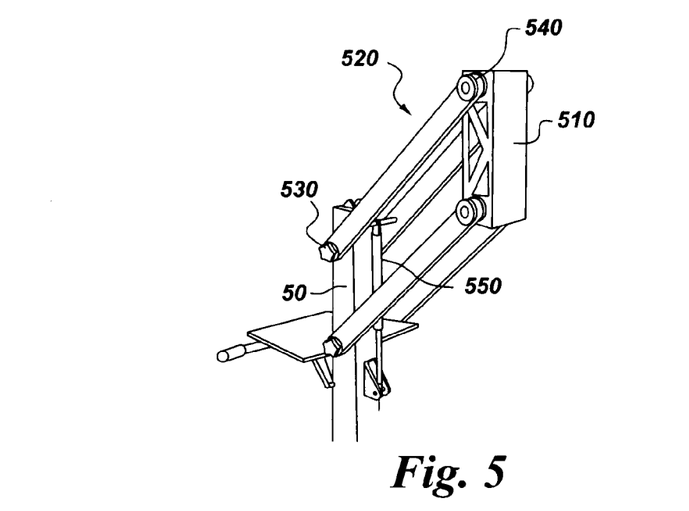
FIG. 5 shows the components of the manipulating arm according to one embodiment.

In FIG. 5, the linkage assembly 55 is detailed according to one embodiment. This example consists of two sets of parallel members 520 that are typically used to roughly orient the imaging unit 65 in the vertical plane. Each member 520 is coupled to the mast 50 by a connector 530. The connector 530 in one example is a rod that extends through a first member, through the mast 50, and through the opposing member such that the rod provides the swinging pivot for the assembly 55 in the vertical plane. In another example, pins are protruding from the sides of the mast 50 where the members 520 are attached. In one embodiment, the arm bracket 510 couples the two (2) parallel four bar mechanisms. The connector 540 in one example is a rod that extends through a first member, through the arm bracket 510, and through the opposing member. In another example, pins are protruding at the connector 540 from the sides of the arm bracket 510 where the members 520 are attached.

In one example, all four of the members 520 are the same, while in another embodiment each pair of members is different. For example, the lower pair of members can have a different cross-section to withstand the load differences between the upper and lower members. In one embodiment the cross section of the linkage is rectangular, another embodiment can be an I-beam or a circular.

The members 520 in one embodiment are square, rectangular or circular shaped, either solid or hollow segments of sufficient material and size to provide the extension capability and handle the torque and stress of the imaging unit. For reference purposes, the segments can be Aluminum or steel. In one embodiment, the rectangular cross section of the hollow aluminum members 520 measures about 0.5-2 in×1-3 in. A circular hollow cross section of about 0.5-2 in in diameter.

In this example, the four members 520 are connected to the mast 50 on one end and joined at the other end by an arm bracket 510. The arm bracket in this example is joined to the linkage assembly 55 by fasteners 540 to each of the members 520. The arm bracket 510 in this embodiment provides the connection to the positioning arm 60 of FIG. 1.

A further optional feature of the linkage assembly 55 is a gas strut 550 attached to the mast to assist the user in moving the imaging unit in the vertical direction with greater ease. Position control is achieved in this example by adjusting the knobs that serve as joints at the bracket 510.

The two (2) parallel four-bar linkage assembly in this example maintains the bracket 510 orientation for all the range of positions, thereby maintaining the orientation of the imaging unit at the end of the positioning arm 60. The two parallel four-bar linkage assembly provides the required stiffness for the torque produced by extension of the positioning arm 60 away from the mast 50.

Figure 6:
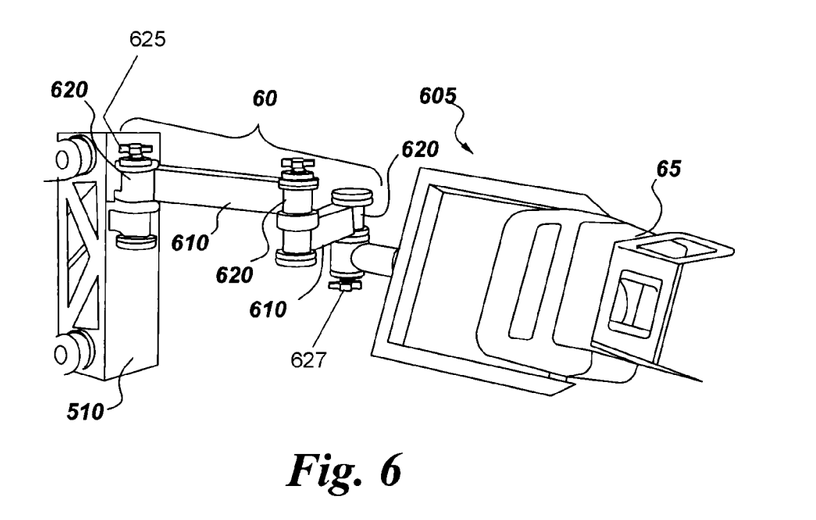
FIG. 6 depicts the flexibility of the positioning arm in one embodiment.

FIG. 6 depicts a configuration of the positioning arm 60 of FIG. 1 according to one embodiment. The positioning arm 60 in this example is positionable with the imaging unit and rotates at multiple degrees of freedom providing a broad range of motion and extension. The positioning arm 60 in this example consists of links 610 with cylindrical joints 620 joining the links. The cylindrical joints 620 in one example are formed by through openings at the end of the links 610 and fastened to securely retain the links 610 but allow rotation about the joint 620. The cylindrical joints 620 in combination provide the desired flexibility and variation typically desired in imaging applications. In the depicted embodiment, the cylindrical joints are configured to provide horizontal rotation. In another example, one or more of the cylindrical joints are oriented to provide rotation in the vertical direction.

There are two links 610 in the illustrated embodiment with three cylindrical joints 620 and two links 610 thereby providing a three member positioning arm 60. In another example there are three links providing further flexibility. In a further example, there is a single link with cylindrical joints on both ends of the link. In addition, one embodiment employs cylindrical joints joining the links but no cylindrical joints on the ends. At the ends of the positioning arm in one example there are fixed attachments, ball joints, or a combination thereof. The links according to one aspect are the same dimensions and length. In another example, the links are different length and/or dimensions.

As shown in FIG. 6, on a first end the positioning arm 60 is coupled to the linkage assembly 55 such as via the arm bracket 510 of FIG. 5. As shown, a cylindrical joint 620 couples the arm bracket 510 to the positioning arm 60. While the cylindrical joint is shown disposed in the horizontal direction, another embodiment disposes this joint to provide rotation in the vertical direction.

On the other end of the positioning arm 60, the imaging source is coupled to the imaging unit bracket 605. In this example, the imaging unit bracket 605 is directly coupled with the cylindrical joint 620 thereby allowing the imaging unit itself to rotate via the cylindrical joint 620. At the end of the links, the source is attached via an imaging unit bracket 605 such as a C-bracket that has fasteners on either side of the imaging unit bracket to securely retain the imaging unit. The imaging unit bracket 605 allows the source to take different orientations for a given location in the space. In a further example, the imaging unit wrist 630 is rotatable thereby allowing the imaging unit bracket 605 to rotate. This rotation of the imaging unit bracket 605 thereby adds yet another flexible orientation of the imaging unit.

As shown in this embodiment, there are three independent pivoting horizontal rotations about cylindrical joints. In one embodiment of these joints, a long pin rotates inside a bushing, either of metal or plastic composition, and secures both members of the joint. In another embodiment, the joint 620 is separated into 3 components comprising of a top bushing between the locking feature and the upper link, an intermediate bushing between the two links and a bottom bushing between the long pin and the bottom link. The rotation about the cylindrical joints 620 in combination with the links 610 allows the positioning arm 60 to retract and extend in the horizontal plane. The multiple cylindrical joints 620 also provide a wide range of angular rotation in the horizontal direction up to almost 360 degrees of rotation with respect to the arm bracket 510. In a further variation, the cylindrical joints 620 are configured to provide a locking mechanism. The locking mechanism in one aspect has certain set locking points such as 90, 180 and 270 degrees that represent the most likely imaging orientations.

Figure 7:
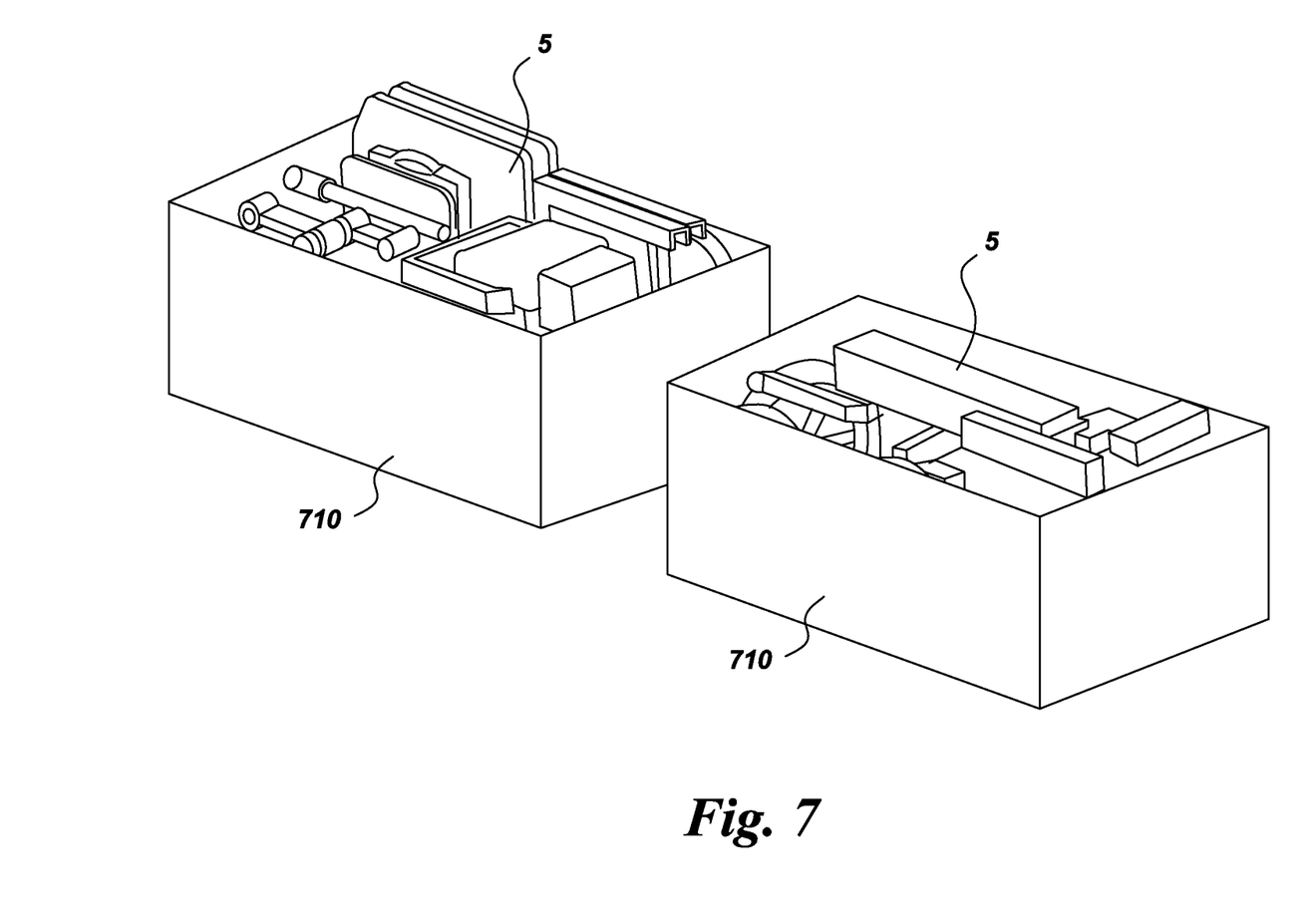
FIG. 7 shows the system configured for transport in accordance with one embodiment.

Storage of the positioner according to one example is shown in FIG. 7. The positioner 5 is designed for easy assembly/disassembly in intuitive, large modules without the necessity of tools. One or more kit containers 710 are packed for easy storage and transportation in rugged, lightweight transport for use anywhere.

For example, one container can accommodate the mast along with the manipulating arm and imaging unit after removal from the cart section. The mast, positioning arm, linkage assembly, and imaging unit are stored in the container without removal and in one example the tray and laptop desk are also stored. The other container is configured to hold the cart section and wheels. In one example, the wheels of the cart assembly can be turned to permit storage without removal, while in another example the wheels are removed without using tools via toolless fasteners, enumerated as 12 in FIG. 8B, and placed into the container. In one example, two foam packed cases are used with a total weight of approximately 160 lb each so that the containers are manageable without requiring machinery. A further example provides for a single container of appropriate size to accommodate the entire unit.

Figure 8A:
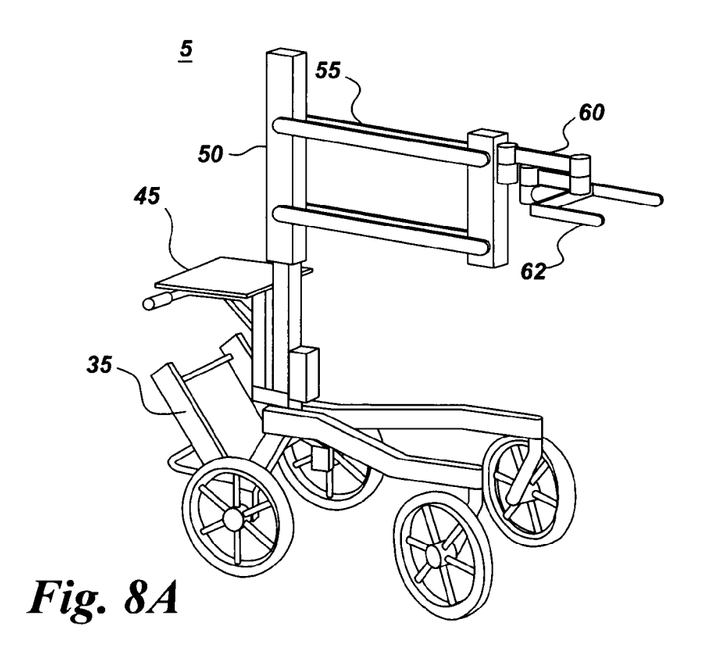
FIG. 8a-8b illustrates an example of the system deployment and disassembly according to one embodiment.
Figure 8B:
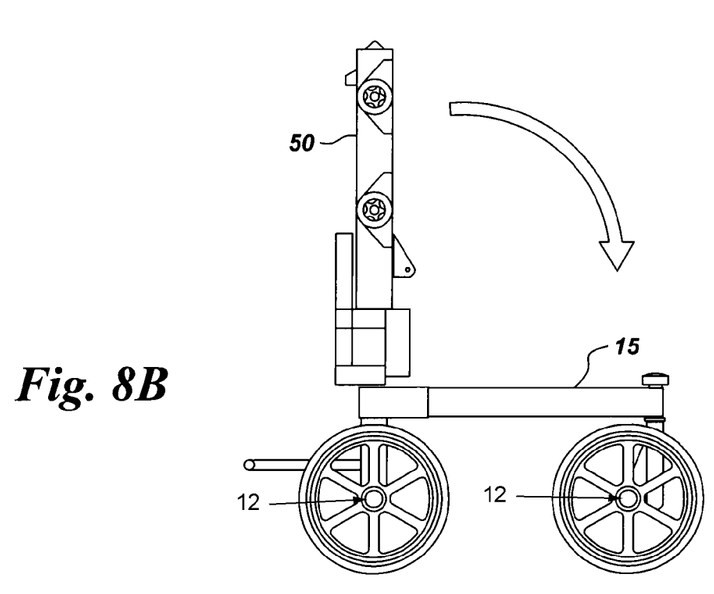

FIGS. 8a-8b shows the imaging system operating in a deployed mode and a storage mode or temporary stowage mode such as for shipping. The imaging unit is not shown as it has been removed via fasteners on the imaging unit bracket 62. In this example, a cylindrical joint is coupled to the imaging unit wrist and therefore the imaging bracket and allows for removal of the imaging bracket by removal of the fastener 627. In this example the imaging bracket is removable from the wrist.

The positioning arm 60 is rotated as shown such that the links are positioned below each other and in a retracted state rather than the extended state. Furthermore, the positioning arm 60 is removable from the linkage assembly 55 via at least one fastener 625 and more particularly from the arm bracket via at least one fastener 625.

The linkage assembly 55 is shown positioned orthogonal to the mast 50. The entire linkage assembly 55 is removable from the mast 50 via the fasteners 530. The spring, if present, is also removable. Furthermore, the desk 45 and holder 35 is also removed in one aspect.

As shown in FIG. 8b, the mast assembly 50 has a joint that provides for rotation such that the mast is tilted such that the mast is oriented approximately parallel to the base frame so the system can be stowed in a compact manner for storage or transport.

Technical advantages of the present disclosed system include portability, maneuverability, adjustability, and flexibility. Regarding portability, the positioner in one example can be packed in two cases, including military grade cases that are stackable, easy to handle and transport. The positioner is designed to be assembled/disassembled by a single person without the need of tools and in a short period of time. And, the positioner can be easily packed and transported to remote medical scenarios. Regarding tool free assembly, various fasteners such as pins and threaded members that typically include self-locking pins and knobs.

The four-wheel cart with front wheels is easy to maneuver over uneven terrain. It can be redeployed quickly from one room to another or from tent to tent without the need of disassembly. It can be moved within a cramped setting, over curbs and minor obstacles by a single operator.

Another characteristic of the system is its ability to position the imaging unit to either side of the positioner and for various imaging shots. The imaging unit is easily adjusted to different positions, at different heights and orientations. A combination of moveable cart, telescoping mast, linkage assembly, positioning arm, and imaging unit bracket adjustments cover all possible configurations around the imaging patient/object. Repositioning for head-to-toe is easily achieved by rolling the positioner, while maintaining the arm and linkage assembly positions. This allows the operator to take images quick without the need of major adjustments to the patient settings. The positioner can be located along the bed, without the need of open space underneath the patient, allowing for greater flexibility. It can be used with any imaging radiation source: x-rays, neutron, gamma, radioisotopes, alpha, and beta.

There are also commercial applications for this positioner as an ambulatory system, used in sporting events, nursing homes, veterinary applications, and applications where an imaging source is needed in a remote location. Space for a battery pack extends its use to locations where no power outlet is available. While there are a number of embodiments, some of the elements of the positioner system as a complete imaging system include the user interface on the portable system for easy use by a lesser trained professional.

Another feature includes the portability wherein there is power conditioning from various power sources allowing for operation and also charging of the system batteries. The batteries provide a completely portable system that can be deployed at least temporarily in very severe environments.

Other features and advantages of the system include flexibility in positioning; AP/LAT and moving from one to the other; virtually any position of tube on half sphere around patient center; head to toe shot; motion from one side of litter to other for best anatomical positioning (no need to be centered); and tomosynthesis ready (motion along long axis of patient for several shots without moving detector) including semi-automated or automated operation.

Other aspects relate to flexibility in gantry positioning on either side of a litter or bed. The small size allows the positioner to fit between litters and through small doors and openings. A further benefit of this system is that all required equipment mounted on gantry. Another feature is the use of large tires for sand and uneven surfaces. In addition, the positioner is stable in various tube positions and park positions for transport.

The transportability of the positioner allows for deployment in many regions and locations. The containerization of the system according to one embodiment is rugged with foam packed containers and the overall system is lightweight with two cases weighing approximately 160 lb each. The self-contained electrical system in one mode operates with 120V outlet operation with centralized power distribution with conditioning, as required.

The system includes a number of features and corresponding enablers that allow for the enhanced features. The small size and lightweight structure is made possible by an optimized footprint, tubular frame, lightweight materials, retractable arms and mast. The stability of the system is accomplished by the multi-wheel cart, larger wheels, and optimized footprint. The positioner has numerous applications and provides capabilities and flexibility for imaging technology. For example, in x-ray system technology for the military applications to provide treatment for injured soldiers in theater. The combination of features provides a compact portable and rugged positioner for the x-ray tube, detector, acquisition system, and peripherals.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A portable positioner, comprising:
    a cart section comprising a base frame removably coupled via collapsible front and rear legs and toolless fasteners to a plurality of wheels, rollers, or combinations thereof, said plurality of wheels, rollers, or combinations thereof resting upon a surface, said front legs collapsible in a counterclockwise direction and said rear legs collapsible in a clockwise direction;
    a mast extending from the cart section and removably connected to the cart section via a toolless coupling at a first end of the mast and oriented approximately orthogonal from the surface;
    a linkage assembly removably coupled via toolless fasteners proximate a second end, located at the top of the mast and configured to swing about in a vertical plane;
    a positioning arm removably coupled via toolless fasteners to the linkage assembly and configured to swing about at least one of a horizontal plane and the vertical plane; and
    an imaging bracket removably coupled via toolless fasteners to the positioning arm and configured to receive an imaging unit.

2. The positioner of claim 1, wherein the linkage assembly comprises two pairs of linkage members having an upper pair of members and a lower pair of members, wherein the upper pair of members and the lower pair of members have substantially similar length and dimensions.

3. The positioner of claim 1, wherein the linkage assembly comprises a parallel linkage system with at least one parallel four bar assembly.

4. The positioner of claim 3, further comprising extra linkage support members.

5. The positioner of claim 1, wherein the positioning arm comprises at least two links and at least two rotatable joints coupling said links.

6. The positioner of claim 5, wherein the rotatable joints are cylindrical joints or locking ball joints.

7. The positioner of claim 1, wherein positioning arm is coupled to the linkage assembly by a rotatable cylindrical joint.

8. The positioner of claim 1, wherein at least one of the mast and positioning arm is configured to telescope.

9. The positioner of claim 1, wherein the plurality of wheels, rollers, or combinations thereof comprises four wheels, rollers, or combinations thereof.

10. The positioner of claim 1, wherein the imaging unit is an x-ray imaging unit, said x-ray imaging unit comprising an x-ray head.

11. The positioner of claim 1, further comprising an imaging unit bracket attached to said positioning arm on a first end and to the imaging device on a second end.

12. The positioner of claim 11, wherein the imaging unit bracket is configured to provide for rotation of the imaging unit in at least one plane.

13. A portable imaging system, comprising:
    a cart section comprising a base frame deployed substantially parallel to a surface;
    a telescoping mast removably attachable to the cart section by a toolless mast coupling, such that said mast extends from the cart section on a first end and is oriented approximately orthogonal from the surface thereby defining a vertical plane and a horizontal plane with reference to said mast and said surface;
    a linkage assembly removably attachable to the telescoping mast by toolless linkage assembly fasteners, such that the linkage assembly comprises two pairs of linkage members opposingly disposed on the mast, said linkage assembly configured to rotate about the vertical plane;
    a positioning arm removably attachable to the linkage assembly by toolless positioning arm fasteners, such that said positioning arm is configured to swing about both the horizontal plane and the vertical plane; and
    an imaging device removably attachable to the positioning arm by toolless imaging device fasteners.

14. The system of claim 13, further comprising four wheels removably coupled to the base frame by toolless wheel fasteners.

15. The system of claim 14, wherein the toolless linkage assembly fasteners, toolless imaging device fasteners, toolless wheel fasteners, and toolless positioning arm fasteners are locking pins or threaded members.

16. The system of claim 13, wherein the two pairs of linkage members comprise an upper pair of members and a lower pair of members, wherein the upper pair of members and the lower pair of members have the same length and dimensions.

17. The system of claim 13, further comprising a gas strut disposed between the linkage assembly and the mast.

18. The system of claim 13, wherein the telescoping mast comprises an inner mast that travels along slides, rollers or bearings.

19. The system of claim 13, packaged in at least one container as a kit, the kit comprising;
the cart section having at least two wheels removably attachable via toolless wheel fasteners to said base frame;
the mast configured to be removably attachable to said cart section by the toolless mast coupling;
the linkage assembly configured to be removably attachable to said mast by the toolless linkage assembly fasteners;
the positioning arm configured to be removably attachable to the linkage assembly by the toolless positioning arm fasteners; and
the imaging device configured to be removably attachable to said positioning arm via toolless imaging device fasteners, wherein the cart section, the mast, the linkage assembly, the positioning arm and the imaging device are individually disposed in said at least one container.

20. A transportable imaging system, comprising:
a cart section with at least one of wheels, rollers or combinations thereof removably attached thereto via toolless fasteners;
a mast receptacle fastened to said cart section;
a mast having a lower end and an upper end, said lower end of the mast removably coupled to said receptacle and extending vertically from the cart section, wherein the mast receptacle forms a toolless coupling with the lower end of the mast;
a waist removably attached via a toolless fastener proximate the upper end of the mast;
a first beam having a first end and a second end, said first end coupled to the waist, wherein the mast is configured to extend vertically;
a shoulder forming a cylindrical joint coupled to the second end of the first beam, said shoulder providing rotation in the horizontal plane;
an elbow forming a cylindrical joint coupled to the shoulder, said elbow allowing for rotation in the vertical plane;
a second beam having a first end and a second end with the first end also coupled to the elbow, said second beam rotatable in a vertical plane;
a wrist coupled to the second end of the second beam, said wrist also coupled to an imaging bracket; and
an imaging source removably coupled via toolless fasteners to the imaging bracket.

21. The system of claim 20, wherein the wrist is a cylindrical joint or locking ball joint.

* * * * *

UNITED STATES PATENT AND TRADEMARK OFFICE
CERTIFICATE OF CORRECTION

PATENT NO. : 8,840,304 B2  
APPLICATION NO. : 12/980392  
DATED : September 23, 2014  
INVENTOR(S) : Perez Zarate et al.

Page 1 of 1

It is certified that error appears in the above-identified patent and that said Letters Patent is hereby corrected as shown below:

In the Specification

In Column 1, Line 56, delete "tools" and insert -- tools. --, therefor.

In Column 2, Line 16, delete "FIG." and insert -- FIGS. --, therefor.

In Column 2, Line 39, delete "FIG. 8a-8b illustrates" and insert -- FIGS. 8a-8b illustrate --, therefor.

In Column 7, Line 36, delete "anterioposterior" and insert -- anterior-posterior --, therefor.

In Column 10, Line 9, delete "shows" and insert -- show --, therefor.

In the Claims

In Column 13, Line 16, in Claim 19, delete "comprising;" and insert -- comprising: --, therefor.

Signed and Sealed this  
Twenty-sixth Day of May, 2015

Michelle K. Lee  
*Director of the United States Patent and Trademark Office*